United States Patent
Barnes et al.

(10) Patent No.: US 9,688,621 B2
(45) Date of Patent: *Jun. 27, 2017

(54) PROCESS FOR PREPARING AN INTERNAL OLEFIN SULFONATE

(71) Applicants: SHELL INTERNATIONALE RESEARCH MAATSCHAPPIJ B.V., Carel van Bylandtlaan (NL); SHELL OIL COMPANY, Houston, TX (US)

(72) Inventors: Julian Richard Barnes, Amsterdam (NL); Hendrik Dirkzwager, Harde (NL); Robert Moene, Amsterdam (NL); Jasper Roelf Smit, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/366,757

(22) PCT Filed: Dec. 21, 2012

(86) PCT No.: PCT/EP2012/076804
§ 371 (c)(1),
(2) Date: Jun. 19, 2014

(87) PCT Pub. No.: WO2013/093075
PCT Pub. Date: Jun. 27, 2013

(65) Prior Publication Data
US 2014/0336409 A1 Nov. 13, 2014

(30) Foreign Application Priority Data
Dec. 23, 2011 (EP) ..................... 11195469

(51) Int. Cl.
C07C 309/00 (2006.01)
C07C 303/22 (2006.01)
C07C 303/06 (2006.01)
C07C 309/20 (2006.01)

(52) U.S. Cl.
CPC .......... *C07C 303/22* (2013.01); *C07C 303/06* (2013.01); *C07C 309/20* (2013.01)

(58) Field of Classification Search
None
See application file for complete search history.

(56) References Cited

U.S. PATENT DOCUMENTS

| | | |
|---|---|---|
| 4,183,867 A | 1/1980 | Sekiguchi et al. |
| 4,248,793 A | 2/1981 | Sekiguchi et al. |
| 5,510,306 A | 4/1996 | Murray |
| 5,633,422 A | 5/1997 | Murray |
| 5,648,584 A | 7/1997 | Murray |
| 5,648,585 A | 7/1997 | Murray et al. |
| 5,849,960 A | 12/1998 | Singleton et al. |
| 2010/0282467 A1 | 11/2010 | Hutchison et al. |

FOREIGN PATENT DOCUMENTS

| | | |
|---|---|---|
| CN | 1039803 | 2/1990 |
| CN | 1053235 | 7/1991 |
| EP | 0351928 | 7/1989 |
| EP | 0351928 | 1/1990 |
| EP | 0446971 | 9/1991 |
| EP | 0830315 | 7/2002 |
| WO | 9506632 | 3/1995 |
| WO | 0064867 | 11/2000 |
| WO | 2010129051 | 11/2010 |

OTHER PUBLICATIONS

Data Sheet for C12 olefin by Shell Chemicals, Nov. 2002, p. 1-.*
Adami; "The Production of α-Olefin Sulfonate by SO3 Sulfonation", Handbook of Detergents, Part F: Production, Section 5.3.1, pp. 102-109, CRC Press, 2009.
Stache, H.W. and Van Os; "Anionic Surfactants: Organic Chemistry", Surfactant Science Series, vol. 56, Chapter 7, Marcel Dekker, Inc., New York, 1996.
Barnes, Julian R., et al.; Application of Internal Olefin Sulfonates and Other Surfactants to EOR. Part 1: Structure—Performance Relationships for Selection at Different Reservoir Conditions, SPE 129766, 2010, pp. 1-16.
State Intellectual Property Office of the People's Republic of China, Ref. TS2727-CN-PCT, 1st Office Action Mar. 27, 2015 for Chinese Application No. 2012800670144.

* cited by examiner

*Primary Examiner* — Fereydoun G Sajjadi
*Assistant Examiner* — Ana Z Muresan

(57) ABSTRACT

The invention relates to a process for preparing an internal olefin sulfonate, comprising sulfonating an internal olefin into sulfonated internal olefin followed by contacting sulfonated internal olefin with a base containing solution, wherein the molar ratio of internal olefin to solvent for the base is higher than 0.06. Further, the invention relates to an internal olefin sulfonate obtainable by said process.

12 Claims, 2 Drawing Sheets

PROCESS FOR PREPARING AN INTERNAL OLEFIN SULFONATE

PRIORITY CLAIM

The present application is the National Stage (§371) of International Application No. PCT/EP2012/076804, filed Dec. 21, 2012, which claims priority from European application no. 11195469.9, filed Dec. 23, 2011, the disclosures of which are incorporated herein by reference.

FIELD OF THE INVENTION

The present invention relates to a process for preparing an internal olefin sulfonate, and to an internal olefin sulfonate obtainable by said process.

BACKGROUND OF THE INVENTION

It is known to use internal olefin sulfonates (IOS) as a surfactant for a variety of applications including chemical Enhanced Oil Recovery (cEOR).

Further, it is known to prepare olefin sulfonates from alpha-olefins and internal olefins, by sulfonating the olefins followed by neutralizing and hydrolyzing the sulfonated olefin containing intermediate mixture which comprises alkene sulfonic acids and sultones that are to be converted into the desired sulfonates. Said neutralization step and subsequent hydrolysis step both comprise contacting sulfonated olefin with a base containing solution, for example an aqueous NaOH containing solution. The hydrolysis step is generally carried out at a higher temperature than the temperature in the neutralization step, and is aimed at completing the reaction of the base with sulfonated olefin. See for example Adami, "The Production of α-Olefin Sulfonate by $SO_3$ Sulfonation", Section 5.3.1, pages 102-109, Handbook of Detergents, Part F: Production, CRC Press, 2009.

Further, EP0351928A1 discloses a process for the preparation of internal olefin sulfonates which comprises reacting in a film reactor an internal olefin having from 8 to 26 carbon atoms with a sulfonating agent, in a mol ratio of sulfonating agent to internal olefin of 1:1 to 1.25:1 while cooling the reactor with a cooling means having a temperature not exceeding 35° C., and allowing to neutralize and hydrolyze the reaction product from the sulfonation step.

More in particular, Example 14 of EP0351928A1 discloses a neutralization step wherein continuous neutralization of sulfonated $C_{15-19}$ internal olefins from the preceding sulfonation step was performed at 30° C., at a residence time of about 20 minutes and at an active matter content of 26-31 wt. %. After the start of the continuous neutralization, a sample was taken after waiting for at least 1 hour and such sample was hydrolyzed for 1 hour at 160° C.

Said sample containing neutralized and hydrolyzed internal olefin sulfonate product from said Example 14 contained 6.7 wt. % of "free oil", part of which (about 2 wt. %) was comprised of paraffins. In the Examples of EP0351928A1, the free oil content is calculated on the amount of active matter. Further, "free oil" is defined therein as "the petroleum ether extractable material in an aqueous-alcoholic solution of internal olefin sulfonates". Therefore, in relation to internal olefin sulfonates, "free oil" may comprise any non-ionic, organic compounds that may be present in an internal olefin sulfonate product.

Such non-ionic compounds in the "free oil" in internal olefin sulfonate products may be unreacted internal olefins that have not been converted into alkene sulfonic acids or sultones. Further, such non-ionic compounds may be internal olefins formed by a back-reaction of sultones into internal olefins and $SO_3$. Still further, such non-ionic compounds may be sultones that have not been converted into sulfonates. Further non-ionic compounds may be sulfonate esters and secondary alcohols formed from such sulfonate esters by saponification.

Additionally, an internal olefin sulfonate product may contain non-ionic compounds that cannot take part in the sulfonation and neutralization reactions. For example, (non-olefinic) paraffins present in the internal olefin feed cannot be sulfonated and therefore end up as non-ionic compounds in the internal olefin sulfonate product.

In general, it is desired to prepare an internal olefin sulfonate having a relatively low free oil content, more in particular having a relatively low content of internal olefins and/or sultones. For such relatively low content means that the sulfonation and neutralization reactions have completed to a greater extent, thereby wasting less valuable starting material and recovering more of the desired sulfonates. Besides, free oil represents a particularly objectionable impurity in the internal olefin sulfonate product, from the standpoint of its influence upon detergency, foaming, color, odor and other physical and chemical properties. There are methods known for removing free oil from final internal olefin sulfonate products after neutralization and hydrolysis. A particular method is for example disclosed in U.S. Pat. No. 4,579,690. However, such additional steps to remove free oil after neutralization and hydrolysis are cumbersome and time consuming. Therefore, it is desired that internal olefin sulfonates are prepared in such a way that the internal olefin sulfonate product itself already has a relatively low free oil content obviating the need for removal of free oil therefrom.

Therefore, the object of the present invention is to provide a process for preparing an internal olefin sulfonate wherein the obtained internal olefin sulfonate product has a relatively low free oil content, more in particular a relatively low content of internal olefins and/or sultones.

SUMMARY OF THE INVENTION

Surprisingly it was found that an internal olefin sulfonate having a relatively low free oil content, more in particular a relatively low content of unreacted internal olefin, can be obtained in a process comprising contacting sulfonated internal olefin with a base containing solution, wherein the molar ratio of internal olefin to solvent for the base is higher than 0.06.

Accordingly, the present invention relates to a process for preparing an internal olefin sulfonate, comprising sulfonating an internal olefin into sulfonated internal olefin followed by contacting sulfonated internal olefin with a base containing solution, wherein the molar ratio of internal olefin to solvent for the base is higher than 0.06.

Further, the present invention relates to an internal olefin sulfonate obtainable by said process.

DETAILED DESCRIPTION OF THE INVENTION

Figure 1A:
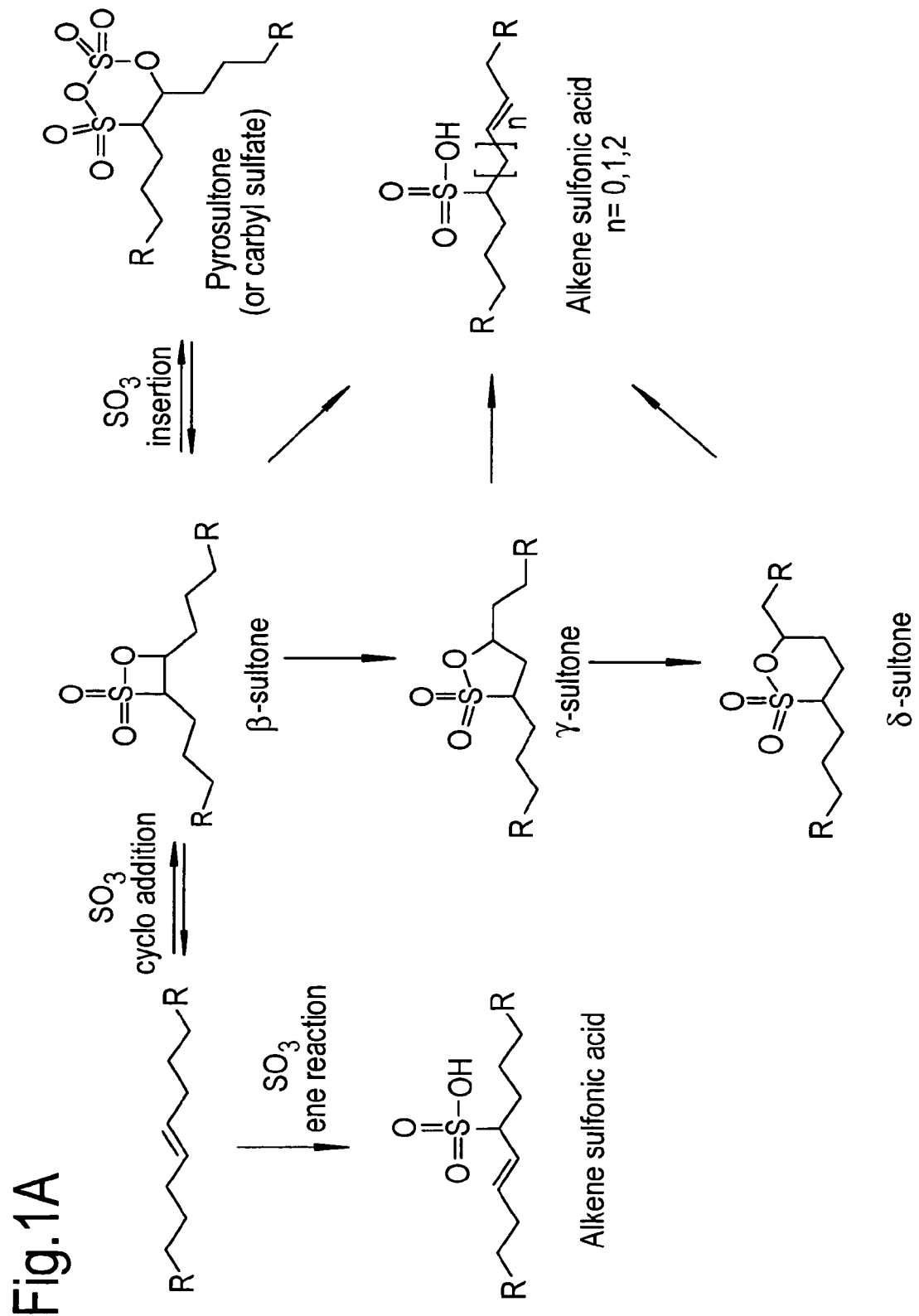
FIG. 1A illustrates the reactions of an internal olefin with sulfur trioxide (sulfonating agent) during a sulfonation process.

In the present invention, after sulfonating the internal olefin into sulfonated internal olefin, the latter is contacted with a base containing solution, wherein the molar ratio of internal olefin to solvent for the base is higher than 0.06.

Such relatively high molar ratio of internal olefin to solvent for the base results in a relatively high active matter content for the internal olefin sulfonate product of the present process because less solvent is present in the latter product.

It is generally recognised that "active matter" in relation to surfactants comprises the surfactant compounds themselves. That is to say, in the case of a composition containing an internal olefin sulfonate surfactant, as in the present invention, the anionic internal olefin sulfonate compounds make up the "active matter" of that composition. Non-active matter components of such composition are for example the "free oil" compounds as described above, an excess amount of base (e.g. NaOH), the solvent (e.g. water) for the base, and inorganic salts (e.g. $Na_2SO_4$). In the present specification, in case a non-ionic surfactant is added as process aid as further discussed below, such non-ionic surfactant is thus not considered part of the "active matter".

After the sulfonation step, upon contact with a base containing solution, the active matter content increases. The final active matter content for the internal olefin sulfonate product can be controlled by varying the amount of solvent (such as water) for said base containing solution. Using a relatively small amount of solvent results in a relatively high active matter content.

It has appeared, as illustrated in the below Examples, that when after making sulfonated internal olefin, the latter is contacted with a base containing solution and the molar ratio of internal olefin to solvent for the base is higher than 0.06, resulting in a relatively high active matter content for the internal olefin sulfonate product of the process, the free oil content in that product is surprisingly low.

Preferably, the molar ratio of internal olefin to solvent for the base is higher than 0.06 to 2 (that is, higher than 0.06 and at most 2), more preferably 0.07 to 1, most preferably 0.08 to 0.50. Said molar ratio of internal olefin to solvent for the base is preferably at least 0.07, more preferably at least 0.08, more preferably at least 0.09, more preferably at least 0.10, more preferably at least 0.11. Said molar ratio of internal olefin to solvent for the base is preferably at most 2, more preferably at most 1, more preferably at most 0.80, more preferably at most 0.60, more preferably at most 0.50, more preferably at most 0.40, more preferably at most 0.35, more preferably at most 0.30, more preferably at most 0.25, more preferably at most 0.20, more preferably at most 0.19, more preferably at most 0.18, more preferably at most 0.17, more preferably at most 0.16, most preferably at most 0.15.

Within the present specification, said "molar ratio of internal olefin to solvent for the base" may mean the molar ratio of internal olefin as fed to the sulfonation step to solvent for the base as fed to the next step wherein sulfonated internal olefin is contacted with a base containing solution. However, said "molar ratio of internal olefin to solvent for the base" may also mean the molar ratio of (sulfonated and any not sulfonated) internal olefin as fed to the step wherein sulfonated internal olefin is contacted with a base containing solution, to solvent for the base as fed to said same step. Normally, both said molar ratios are the same, except in a case wherein sulfonated internal olefin and/or any not sulfonated internal olefin is removed between the sulfonation step and the next step. However, preferably, sulfonated internal olefin from the sulfonation step of the present process is directly, without removing any molecules, subjected to the reaction with the base.

Thus, by increasing the molar ratio of internal olefin to solvent for the base, the active matter content for the internal olefin sulfonate product of the present process is also increased. Preferably, the active matter content for the internal olefin sulfonate product of the present process is 40 to 90 wt. %, more preferably 50 to 85 wt. %, most preferably 55 to 85 wt. %. Said active matter content is preferably at least 35 wt. %, more preferably at least 40 wt. %, more preferably at least 45 wt. %, more preferably at least 50 wt. %, more preferably at least 55 wt. %, more preferably at least 60 wt. %, more preferably at least 65 wt. %, most preferably at least 70 wt. %. Said active matter content is preferably at most 90 wt. %, more preferably at most 85 wt. %, most preferably at most 80 wt. %.

In the present invention, sulfonated internal olefin is contacted with a base containing solution. Within the present specification, "base containing solution" implies that the base is dissolved in a solvent, thereby forming said solution, when the base is contacted with sulfonated internal olefin. Said solvent is thus a solvent for the base.

In the present invention, wherein the molar ratio of internal olefin to solvent for the base that is added after the sulfonation step is relatively high resulting in an internal olefin sulfonate product having a relatively high active matter content, care should be taken that in the reaction of the base with sulfonated internal olefin, the mobility of the reaction mixture is sufficiently high for it to be handled well enough (e.g. in terms of storage, pumping, mass transfer). For example, in the present invention, the mobility of the above-mentioned reaction mixture may be increased by adding a non-ionic surfactant. The use of non-ionic surfactants as such process aid during the present process of making (anionic) internal olefin sulfonate surfactants is further described below. In the present invention, however, advantageously no viscosity modifier needs to be added, such as a non-ionic alkoxylate of an alcohol containing on average 1 to 6, suitably 1 to 3, more suitably 1 to 2, alkoxylate units (preferably ethoxylate units), said alcohol containing on average 1 to 6, suitably 2 to 5, more suitably 3 to 5, carbon atoms. An example of such viscosity modifier is "butylcellosolve" which is 2-butoxy-ethanol. Thus, preferably, the process of the present invention is performed in the absence of a viscosity modifier as defined hereinbefore.

The process of the present invention is a process for preparing an internal olefin sulfonate (IOS) from an internal olefin. Within the present specification, an internal olefin and an IOS comprise a mixture of internal olefin molecules and a mixture of IOS molecules, respectively. That is to say, within the present specification, "internal olefin" as such refers to a mixture of internal olefin molecules whereas "internal olefin molecule" refers to one of the components from such internal olefin. Analogously, within the present specification, "IOS" or "internal olefin sulfonate" as such refers to a mixture of IOS molecules whereas "IOS molecule" or "internal olefin sulfonate molecule" refers to one of the components from such IOS.

Branched IOS molecules are IOS molecules derived from internal olefin molecules which comprise one or more branches. Linear IOS molecules are IOS molecules derived from internal olefin molecules which are linear, that is to say which comprise no branches (unbranched internal olefin molecules). An internal olefin may be a mixture of linear internal olefin molecules and branched internal olefin molecules. Analogously, an IOS may be a mixture of linear IOS molecules and branched IOS molecules.

Within the present specification, an internal olefin or IOS may be characterised by its carbon number, branched content and/or molecular weight. In case reference is made to an average carbon number, branched content and/or average molecular weight, this means that the internal olefin or IOS in question is a mixture of molecules which differ from each other in terms of carbon number, being branched or unbranched and/or molecular weight.

Within the present specification, said average carbon number is determined by multiplying the number of carbon atoms of each internal olefin molecule or IOS molecule by the weight fraction of that molecule and then adding the products, resulting in a weight average carbon number. The average carbon number may be determined by $^{13}C$ NMR analysis or GC analysis.

Within the present specification, said branched content is determined by dividing the amount of branched molecules by the total amount of branched and unbranched molecules. The branched content may be determined by $^{13}C$ NMR analysis or GC analysis.

Within the present specification, said average molecular weight is determined by multiplying the molecular weight of each internal olefin molecule or IOS molecule by the mole fraction or weight fraction of that molecule and then adding the products, resulting in a number average or weight average molecular weight, respectively. The molecular weight may be determined by GC analysis In the present invention, an internal olefin sulfonate is prepared from an internal olefin in a process comprising at least 2 consecutive steps: sulfonation followed by reaction with a base.

In the sulfonation step of the present process, an internal olefin is sulfonated. In the present invention, the internal olefin may have an average carbon number of from 5 to 40, suitably 10 to 35, more suitably 15 to 30, more suitably 18 to 24, more suitably 20 to 24, most suitably 20 to 22.

Further, in the present invention, the branched content of the internal olefin used in the sulfonation step may be of from 0.1 to 30 wt. %, preferably 0.5 to 25 wt. %, more preferably 1 to 20 wt. %, most preferably 2 to 15 wt. %. Branches in the above-mentioned internal olefin molecules may include methyl, ethyl and/or higher molecular weight branches including propyl branches.

In the present invention, the number average molecular weight for the internal olefin may vary within wide ranges, such as from 100 to 500, suitably 150 to 450, more suitably 200 to 400 g/mole, most suitably 250 to 350 g/mole.

An IOS molecule is made from an internal olefin molecule whose double bond is located anywhere along the carbon chain except at a terminal carbon atom. Internal olefin molecules may be made by double bond isomerization of alpha-olefin molecules whose double bond is located at a terminal position. Generally, such isomerization results in a mixture of internal olefin molecules whose double bonds are located at different internal positions. The distribution of the double bond positions is mostly thermodynamically determined. Further, that mixture may also comprise a minor amount of non-isomerized alpha-olefins. Still further, because the starting alpha-olefin may comprise a minor amount of paraffins (non-olefinic alkanes), the mixture resulting from alpha-olefin isomerization may likewise comprise that minor amount of unreacted paraffins.

In the present invention, the amount of alpha-olefins in the internal olefin may be up to 5%, for example 1 to 4 wt. % based on total composition. Further, in the present invention, the amount of paraffins in the internal olefin may be up to 2 wt. %, for example up to 1 wt. % based on total composition.

Suitable processes for making an internal olefin include those described in U.S. Pat. No. 5,510,306, U.S. Pat. No. 5,633,422, U.S. Pat. No. 5,648,584, U.S. Pat. No. 5,648,585, U.S. Pat. No. 5,849,960, EP0830315B1 and "Anionic Surfactants: Organic Chemistry", Surfactant Science Series, volume 56, Chapter 7, Marcel Dekker, Inc., New York, 1996, ed. H. W. Stacke.

In the sulfonation step of the present process, the internal olefin is contacted with a sulfonating agent. Referring to FIG. 1A, reaction of the sulfonating agent with an internal olefin leads to the formation of cyclic intermediates known as beta-sultones, which can undergo isomerization to unsaturated sulfonic acids and the more stable gamma- and delta-sultones.

In the present invention, the sulfonating agent may be sulfur trioxide ($SO_3$), sulfuric acid or oleum. Further, in the present invention, the mole ratio of sulfonating agent to internal olefin may be 0.5:1 to 2:1, more suitably 0.8:1 to 1.8:1, most suitably 1:1 to 1.6:1.

In case sulfur trioxide is the sulfonating agent in the present process, the sulfur trioxide is preferably provided as a gas stream comprising a carrier gas and the sulfur trioxide. The carrier gas may be air or an inert gas, such as nitrogen. The concentration of sulfur trioxide in said gas stream may be 1 to 10 vol. %, more suitably 2 to 8 vol. %, most suitably 3 to 7 vol. %, based on the volume of the carrier gas.

The sulfonation reaction with $SO_3$ is preferably carried out in a film reactor, for example a "falling-film reactor", where the olefin feed is continuously fed onto the inside surfaces of a tube and gaseous $SO_3$ is fed into the tube to react with the (falling) olefin film in a controlled manner. The reactor may be cooled with a cooling means, which is preferably water, having a temperature preferably not exceeding 90° C., especially a temperature in the range of from 10 to 70° C., more suitably 20 to 60° C., most suitably 20 to 55° C., for example by flowing the cooling means at the outside walls of the reactor.

The present process may be carried out batchwise, semi-continuously or continuously, preferably continuously. In particular, the sulfonation step may be carried out batchwise, semi-continuously or continuously. Preferably, the sulfonation step is carried out continuously.

As mentioned above, preferably, sulfonated internal olefin from the sulfonation step of the present process is directly, without removing any molecules, subjected to the reaction with the base. However, between the sulfonation step and the step wherein contacting with a base containing solution is performed in accordance with the present invention, there may still be an intermediate step. Such intermediate step may for example be a step what is generally referred to as "aging", which is commercially applied in the manufacture of alpha-olefin sulfonates. Such aging step may be performed in a way as described by Van Os et al. in "Anionic Surfactants: Organic Chemistry", Surfactant Science Series 56, ed. Stacke H. W., 1996, Chapter 7: Olefin sulfonates, pages 368-369, the disclosure of which is incorporated herein by reference.

Figure 1B:
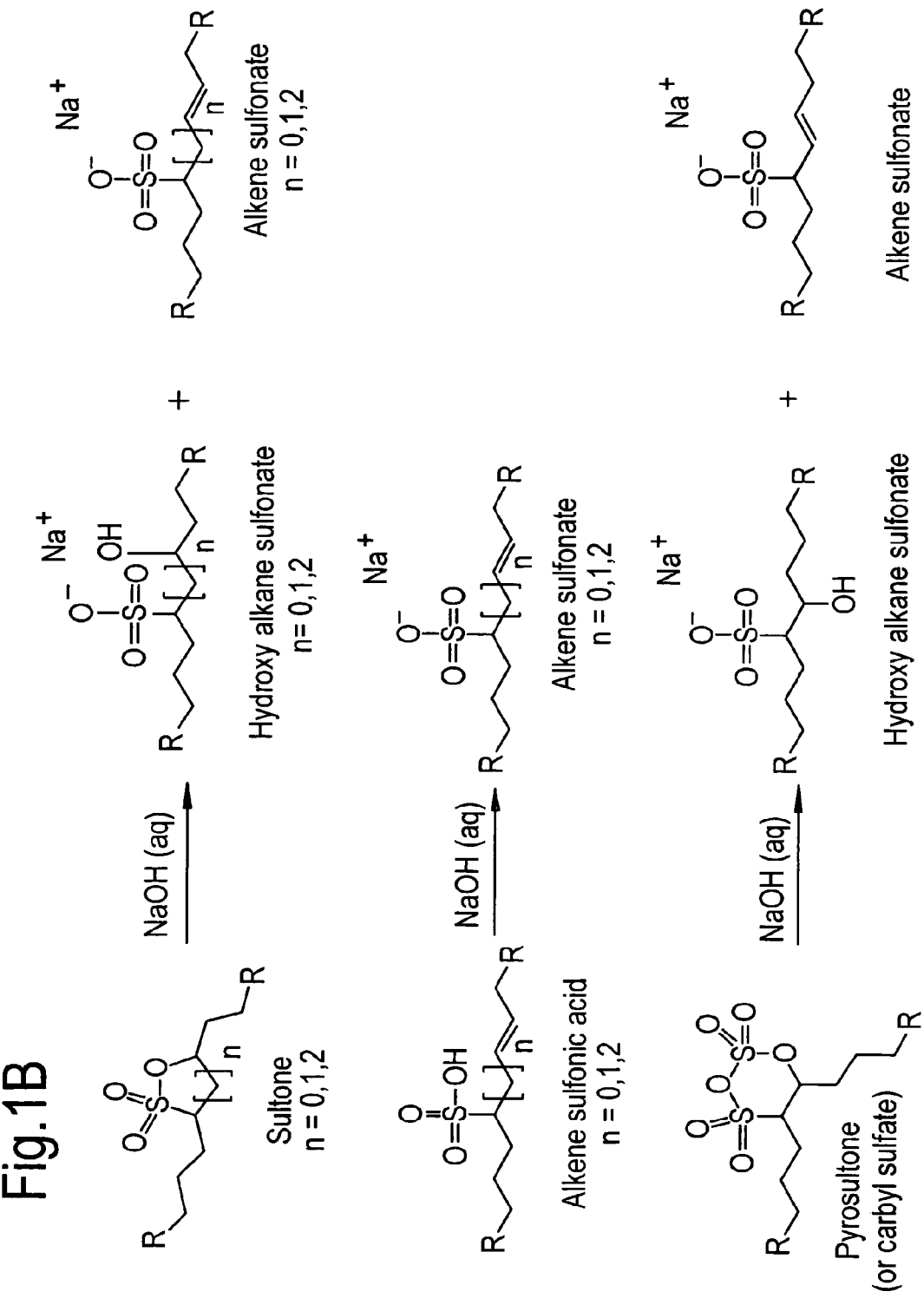
FIG. 1B illustrates the subsequent neutralization and hydrolysis process to form an internal olefin sulfonate.

In the next step of the present process, sulfonated internal olefin from the sulfonation step is contacted with a base containing solution. Referring to FIG. 1B, in this step, beta-sultones are converted into beta-hydroxyalkane sulfonates, whereas gamma- and delta-sultones are converted into gamma-hydroxyalkane sulfonates and delta-hydroxyalkane sulfonates, respectively. Part of said hydroxyalkane sulfonates may be dehydrated into alkene sulfonates.

Thus, referring to FIGS. 1A and 1B, an IOS comprises a range of different molecules, which may differ from one another in terms of carbon number, being branched or unbranched, number of branches, molecular weight and number and distribution of functional groups such as sulfonate and hydroxyl groups. An IOS comprises both hydroxyalkane sulfonate molecules and alkene sulfonate molecules and possibly also di-sulfonate molecules. Hydroxyalkane sulfonate molecules and alkene sulfonate molecules are shown in FIG. 1B. Di-sulfonate molecules (not shown in FIG. 1B) originate from a further sulfonation of for example an alkene sulfonic acid as shown in FIG. 1A.

The base to be contacted with sulfonated internal olefin from the sulfonation step may be a water soluble base, which is preferably selected from the group consisting of hydroxides, carbonates and bicarbonates of an alkali metal ion, such as sodium or potassium, or of an earth alkali metal ion, or of ammonium ion, and amine compounds. Suitable examples are sodium hydroxide and sodium carbonate, most suitably sodium hydroxide. Further, preferably, the solvent for the base is water. Preferably, in this step, sulfonated internal olefin is contacted with an aqueous solution of a water soluble base, such as described hereinabove, especially sodium hydroxide.

The reaction in this step is generally carried out with an excessive molar amount of base. It is preferred that the final internal olefin sulfonate product is not acidic because this may lead to corrosion of process equipment and/or to disintegration of the internal olefin sulfonate. Therefore, it is preferred that the final internal olefin sulfonate product contains a certain amount of base, for example 0.1 to 2 wt. % based on 100% of the active matter. This may be achieved by choosing the amount of base to be added such that the molar ratio of (i) the amount of base fed to the step wherein sulfonated internal olefin is contacted with the base containing solution to (ii) the amount of sulfonating agent (e.g. $SO_3$) fed to the sulfonation step is higher than 1, suitably higher than 1 up to 1.4, more suitably 1.1 to 1.3.

The base and the solvent for the base may be added separately. Preferably, the base is added as part of a solution as described above. Additional solvent may be added separately in addition to such base containing solution. If the base is added as part of a solution, the concentration of the base in such solution, based on total solution, is suitably at most 60 wt. %, more suitably 10 to 55 wt. %, most suitably 20 to 55 wt. %.

The temperature at which sulfonated internal olefin is contacted with the base containing solution in the present process may vary within wide ranges, for example 0 to 250° C. Further, the time for the reaction between the base and sulfonated internal olefin may also vary within wide ranges, for example 5 minutes to 4 hours.

In the step wherein sulfonated internal olefin is contacted with the base containing solution, a non-ionic surfactant may also be added as a process aid. Preferably, the non-ionic surfactant is an alkoxylate of an alcohol having an aliphatic group, preferably an ethoxylate of such alcohol. Said alcohol may be primary or secondary, preferably primary. Said alcohol alkoxylate may be of the following formula:

R—O—[R'—O]$_x$—H          (I)

wherein R is the aliphatic group originating from the alcohol, R'—O is an alkylene oxide group, and x represents the number of such alkylene oxide groups.

The non-ionic surfactant of above exemplary formula (I) comprises a range of different molecules which may differ from one another in terms of carbon number for the aliphatic group R, the aliphatic group R being branched or unbranched (linear), nature and number of alkylene oxide groups R'—O, and molecular weight. Thus, the non-ionic surfactant of above exemplary formula (I) comprises a mixture of surfactant molecules. That is to say, within the present specification, "surfactant" as such refers to a mixture of surfactant molecules whereas "surfactant molecule" refers to one of the components from such surfactant.

The weight average carbon number for the aliphatic group R from the optional non-ionic surfactant of above exemplary formula (I) is not essential and may vary within wide ranges, such as from 4 to 25, suitably 6 to 20, more suitably 8 to 15. Further, preferably, said aliphatic group is linear.

The alkylene oxide groups R'—O in above exemplary formula (I) may comprise any alkylene oxide groups. For example, said alkylene oxide groups may comprise ethylene oxide groups, propylene oxide groups and butylene oxide groups or a mixture thereof, such as a mixture of ethylene oxide and propylene oxide groups. In case of a mixture of ethylene oxide and propylene oxide groups, the mixture may be random or blockwise. Preferably, said alkylene oxide groups consist of ethylene oxide groups.

In above exemplary formula (I), x represents the number of alkylene oxide groups R'—O. In the present invention, for the optional non-ionic surfactant of above exemplary formula (I), the average value for x is at least 0.5. Said average value for x may be of from 1 to 20, more suitably 4 to 16, most suitably 7 to 13.

Further, the number average molecular weight for the optional non-ionic surfactant of above exemplary formula (I) may be 300 to 700 g/mole, more suitably 400 to 600 g/mole, most suitably 450 to 550 g/mole.

As mentioned above, such non-ionic surfactant may increase mobility, thereby improving intimate mixing of the product from the sulfonation step with the base containing solution. In such way, contact between the organic phase and the base containing aqueous phase is improved. This improves mass transfer and promotes the desired reaction of the sultones and alkene sulfonic acids with the base, and avoids as much as possible the reverse reaction of beta-sultones into internal olefins and $SO_3$. Alternatively or additionally, this may be achieved by efficient stirring or by the addition of a co-solvent (such as a lower alcohol).

The step wherein sulfonated internal olefin is contacted with the base containing solution may be carried out batchwise, semi-continuously or continuously. Preferably, said step is carried out continuously. Further, a continuously stirred tank reactor (CSTR; e.g. a loop reactor) and/or a plug flow reactor may be used in this step.

The step of the present process wherein sulfonated internal olefin is contacted with a base containing solution may be carried out as 2 separate, consecutive steps: a "neutralization step" followed by a "hydrolysis" step. In the present specification, "neutralization step" means the step wherein sulfonated internal olefin from the sulfonation step is contacted with a base containing solution for the first time. Further, in the present specification, "hydrolysis step" means the step that may follow after the former "neutralization step". The above features equally apply to said neutralization step and hydrolysis step separately.

In the present invention, the neutralization step may be carried out batchwise or continuously. Preferably, the neutralization step is carried out continuously. Preferably, a CSTR (e.g. a loop reactor) is used in the neutralization step. The hydrolysis step may also be carried out batchwise or continuously. Preferably, the hydrolysis step is carried out continuously. Preferably, a plug flow reactor is used in the hydrolysis step.

The neutralization step is preferably carried out at a temperature in the range of from 0 to 90° C., more preferably 10 to 80° C., more preferably 20 to 70° C., most preferably 30 to 60° C. The neutralization time may be 5 minutes to 4 hours.

Preferably, the product from the neutralization step is directly, without extracting unreacted internal olefin molecules and without removing the base and solvent, subjected to hydrolysis.

In the hydrolysis step, the product from the neutralization step is further reacted through conversion into sulfonate compounds. Said hydrolysis step is therefore preferably carried out at an elevated temperature, for example in order to convert sultones, especially delta-sultones, into active matter. Preferably, the temperature in the hydrolysis step is higher than the temperature in the neutralization step. Preferably, the temperature in the hydrolysis step is higher than 90 to 250° C., more preferably 95 to 220° C., more preferably 100 to 190° C., most preferably 140 to 180° C. The hydrolysis time may be 5 minutes to 4 hours.

U.S. Pat. No. 4,183,867, U.S. Pat. No. 4,248,793 and EP0351928A1, the disclosures of all of which are incorporated herein by reference, disclose processes which can be used to make internal olefin sulfonates in the process of the present invention. Further, the internal olefin sulfonates may be synthesized in a way as described by Van Os et al. in "Anionic Surfactants: Organic Chemistry", Surfactant Science Series 56, ed. Stacke H. W., 1996, Chapter 7: Olefin sulfonates, pages 367-371, the disclosure of which is incorporated herein by reference.

After reaction of sulfonated internal olefin with the base in accordance with the present invention, the internal olefin sulfonate (IOS) product may be diluted, for example by adding additional solvent (e.g. water), for example in case one wishes to facilitate the handling of that product in the application for which the IOS product is intended.

The invention is further illustrated by the following Examples.

EXAMPLES

General Experimental Set-Up

In the present Examples, sulfonation, neutralization and hydrolysis of the internal olefin feedstock in question were carried out in a continuous process.

Sulfonation was carried out in a falling-film reactor. The reactor length (L) was 6 meters and the reactor diameter (d) was 1 inch (2.54 cm). The sulfonating agent was $SO_3$ that was generated in situ by burning sulphur to $SO_2$ using dried air and converting the $SO_2$ from the air stream into $SO_3$ in a catalyst bed. Both said air stream, containing 5 vol. % of $SO_3$, and the internal olefin feedstock were then fed to the sulfonation reactor at an inlet temperature of 30° C. The molar ratio of $SO_3$ fed to the reactor to olefin fed to the reactor was higher than 1:1, and was varied by varying the amount of olefin fed. The $SO_3$ feedstream was maintained at 6 kg/hour in all experiments. Said molar ratio was either 1.06 or 1.30. The reactor was cooled with cooling water having a temperature of 30° C.

Neutralization was carried out in a loop reactor having a volume of 24 liters. A pump was used to circulate the mixture from the sulfonation reactor through said loop reactor. The base used was NaOH, which was added to the loop reactor in the form of an aqueous NaOH solution. The NaOH concentration in said solution was either 30 wt. % or 50 wt. %, based on total amount of the solution. The amount of NaOH fed to the neutralization reactor was such that the molar ratio of NaOH fed to the neutralization reactor to $SO_3$ fed to the sulfonation reactor amounted to 1.20. Either additional water was added, in addition to the water from said NaOH solution, or no additional water was added. The total amount of water in the base containing solution added and additional water added (if any) were such that the molar ratio of olefin fed to the sulfonation reactor to total water fed to the neutralization reactor was either higher than 0.06 (in accordance with the invention) or lower than 0.06 (comparative). The temperature during neutralization was 50° C. By reducing the amount of total water fed to the neutralization reactor, the residence time for the reaction mixture in the neutralization reactor is increased.

In addition, a non-ionic surfactant was added during neutralization in an amount of either 5 or 10 wt. % (based on 100% of active matter). The non-ionic surfactant added was NEODOL™ 91-8 (hereinafter abbreviated as "N91-8"). N91-8 is an ethoxylate of NEODOL™ 91 which is a blend of mainly C9, C10 and C11 linear primary alcohols (C8 and lower=<1 wt. %; C9=18 wt. %; C10=42 wt. %; C11=38 wt. %; C12 and higher=1 wt. %; weight average carbon number=10.20). N91-8 comprises 8 ethoxylate units and has a number average molecular weight of about 513.

Hydrolysis was carried out in a non-stirred plug flow reactor, having a volume of 40 liters, to which the mixture from the neutralization reactor was fed directly. Water was neither added nor removed from the mixture. By reducing the amount of total water fed to the neutralization reactor, the residence time for the reaction mixture in the hydrolysis reactor is also increased. The temperature during hydrolysis was either 150 or 170° C.

Properties of Internal Olefin Feed

Two types of internal olefin feedstocks were used, herein designated as "internal olefin I" and "internal olefin II". Both said feedstocks were mixtures comprising only even carbon number internal olefin molecules, obtained by double bond isomerization of even carbon number alpha-olefins. In addition, the internal olefin feedstocks contained small amounts of paraffins and/or alpha-olefins. Properties of these feedstocks are shown in Table 1 below.

TABLE 1

|  | Internal olefin I | Internal olefin II |
| --- | --- | --- |
| Composition in terms of carbon number (wt. %) |  |  |
| C16 | 0.10 | 0.06 |
| C18 | 2.60 | 4.53 |
| C20 | 70.08 | 63.32 |
| C22 | 22.46 | 27.59 |
| C24 | 4.14 | 3.75 |
| C26 | 0.48 | 0.64 |
| C28 | 0.14 | 0.11 |
| C30 | 0.01 | <0.01 |
| Weight average carbon number | 20.60 | 20.66 |
| Number average molecular weight (g/mole) | 287.40 | 288.05 |
| Alpha-olefins[1] (wt. %) | 1.5 | 3 |
| Paraffins[1] (wt. %) | 0.07 | below detection limit |
| Branched content[2] (wt. %) | 9 | 3.2 |

[1]Based on total composition.
[2]"Branched content" = amount of branched molecules based on total amount of branched and linear molecules.

Product Components in Samples

During the experiments, a sample of the mixture exiting the neutralization reactor prior to entering the hydrolysis reactor was taken, which was then analyzed. As the neutralization step was carried out continuously in a loop reactor, said sample is also representative for the mixture inside that reactor. Further, a sample of the mixture exiting the hydrolysis reactor was taken, which was then also analyzed. The analyzed product properties were:

1. Active matter (AM) content (wt. % on 100% mixture): content of anionic internal olefin sulfonate molecules. The AM content was determined by a method involving a titration with HYAMINE™ titrant. The basic principles of the method are described in "Introduction to surfactant analysis", edited by D.C. Column, page 60, 1994. Further, AM content may be determined by the ASTM D6173 and ISO 2271 methods.

2. Free oil content (wt. % on 100% AM): content of non-ionic (organic) molecules, excluding the above-mentioned non-ionic N91-8 surfactant. Said free oil content was determined by a method involving High Pressure Liquid Chromatography (HPLC), thereby separating neutral compounds from the ionic compounds, and then correcting the obtained value for the amount of said N91-8. Further, free oil content may be determined by the ASTMD D3673 method.

3. NaOH content (wt. % on 100% AM): The NaOH content may be determined by titration with an acid (for example HCl).

4. $Na_2SO_4$ content (wt. % on 100% AM): The $Na_2SO_4$ content may be determined by the ASTM D6174 method.

Examples 1 and 2 and Comparative Examples 1-3

In Examples 1 and 2 and Comparative Examples 1-3, the internal olefin feedstock was above-described internal olefin I. The experiments were performed as described above. Further process parameters and product components are shown in Table 2 below.

Example 1 and Comparative Example 1 differ from each other in terms of the AM content (75 wt. % and 31 wt. %, respectively) and the hydrolysis temperature (150° C. and 170° C., respectively). Surprisingly, the free oil content for Example 1 (2.91) was substantially lower than that for Comparative Example 1 (6.12). Comparative Example 2 also shows the negative effect of a lower AM content (also 31 wt. %) on the free oil content (5.92)

Example 2 and Comparative Example 3 differ from each other in terms of the AM content (73 wt. % and 28 wt. %, respectively), the hydrolysis temperature (150° C. and 170° C., respectively) and the amount of N91-8 added during neutralization (5% and 10%, respectively). However, also in this case, the free oil content for Example 2 (3.80) was substantially lower than that for Comparative Example 3 (11.20).

Examples A and B and Comparative Example C

In Examples A and B and Comparative Example C, the internal olefin feedstock was above-described internal olefin II. The experiments were performed as described above. Further process parameters and product components are shown in Table 2 below.

Example A and Comparative Example C differ from each other in terms of the AM content (72 wt. % and 30 wt. %, respectively). Surprisingly, the free oil content for Example A (3.43) was substantially lower than that for Comparative Example C (10.24). Example B also shows the positive effect of a higher AM content (73 wt. %) on the free oil content (4.81).

TABLE 2

| | SULFONATION | | | NEUTRALIZATION | |
|---|---|---|---|---|---|
| | Olefin feed, kg/hour | $SO_3$/olefin[1], mole/mole | NaOH concentration, wt. %[2] | Extra water fed, in addition to water from NaOH solution? | Olefin fed to sulfonation/total water fed to neutralization[3], mole/mole |
| Ex. 1 | 16.85 | 1.30 | 50 | No | 0.13 |
| Ex. 2 | 20.33 | 1.06 | 50 | No | 0.12 |
| Comp. Ex. 1 | 16.85 | 1.30 | 30 | Yes | 0.02 |
| Comp. Ex. 2 | 16.85 | 1.30 | 30 | Yes | 0.02 |
| Comp. Ex. 3 | 20.33 | 1.06 | 30 | Yes | 0.02 |
| Ex. A | 20.38 | 1.06 | 50 | No | 0.12 |
| Ex. B | 20.38 | 1.06 | 50 | No | 0.12 |
| Comp. Ex. C | 20.38 | 1.06 | 30 | Yes | 0.02 |

Ex. = Example; Comp. Ex. = Comparative Example
[1]"$SO_3$/olefin" = $SO_3$ fed to sulfonation/olefin fed to sulfonation
[2]Based on total amount of aqueous NaOH solution fed to neutralization
[3]"Total water" = water from NaOH solution + any extra water, both fed to neutralization

| | NEUTRALIZATION | | | HYDROLYSIS | |
|---|---|---|---|---|---|
| | N91-8, wt. % on 100% AM | Residence time, minutes | AM, wt. %[1] | Temperature, ° C. | Residence time, minutes |
| Ex. 1 | 10 | 40 | 58.62 | 150 | 60 |
| Ex. 2 | 10 | 40 | 69.96 | 150 | 60 |
| Comp. Ex. 1 | 10 | 20 | 26.85 | 170 | 30 |
| Comp. Ex. 2 | 5 | 20 | 25.61 | 170 | 30 |
| Comp. Ex. 3 | 5 | 20 | 22.50 | 170 | 30 |
| Ex. A | 5 | 40 | 66.48 | 170 | 60 |
| Ex. B | 10 | 40 | 68.36 | 170 | 60 |
| Comp. Ex. C | 5 | 20 | n.d. | 170 | 30 |

Ex. = Example; Comp. Ex. = Comparative Example; AM = active matter; n.d. = not determined
[1]Based on total amount of product from neutralization TABLE 2-continued

| | AM, wt. %[1] | Free oil[2], wt. % on 100% AM | NaOH, wt. % on 100% AM | Na$_2$SO$_4$, wt. % on 100% AM |
|---|---|---|---|---|
| Ex. 1 | 75.20 | 2.91 | 0.35 | 6.18 |
| Ex. 2 | 72.84 | 3.80 | 0.63 | 3.13 |
| Comp. Ex. 1 | 31.26 | 6.12 | 5.73 | 6.37 |
| Comp. Ex. 2 | 31.42 | 5.92 | 5.38 | 7.38 |
| Comp. Ex. 3 | 28.27 | 11.20 | 1.66 | 5.52 |
| Ex. A | 72.38 | 3.43 | 0.23 | 2.25 |
| Ex. B | 72.51 | 4.81 | 0.84 | 2.52 |
| Comp. Ex. C | 29.60 | 10.24 | 1.82 | 5.78 |

Ex. = Example; Comp. Ex. = Comparative Example; AM = active matter
[1]Based on total amount of product from hydrolysis
[2]Free oil content is exclusive of N91-8

That which is claimed is:

1. A process for preparing an internal olefin sulfonate, comprising sulfonating an internal olefin into sulfonated internal olefin followed by contacting sulfonated internal olefin with a base containing solution, wherein the molar ratio of internal olefin to solvent for the base is higher than 0.06, which process is performed in the absence of a viscosity modifier.

2. The process according to claim 1, wherein the molar ratio of internal olefin to solvent for the base is higher than 0.06 to 2.

3. The process according to claim 1, wherein the active matter content for the internal olefin sulfonate product of the process is 40 to 90 wt.

4. The process according to claim 1, wherein the average carbon number of the internal olefin is from 5 to 40.

5. The process according to claim 1, which is carried out continuously.

6. The process according to claim 1, wherein the base is a water soluble base and the solvent for the base is water.

7. The process according to claim 6, wherein the water soluble base is selected from the group consisting of hydroxides, carbonates and bicarbonates of an alkali metal ion, such as sodium or potassium, or of an earth alkali metal ion, or of ammonium ion, and amine compounds.

8. The process according to claim 7, wherein the water soluble base is sodium hydroxide.

9. The process according to claim 1, wherein the temperature at which sulfonated internal olefin is contacted with the base containing solution is 0 to 250° C.

10. The process according to claim 1, wherein in the step wherein sulfonated internal olefin is contacted with the base containing solution, a non-ionic surfactant is added.

11. The process according to claim 10, wherein the non-ionic surfactant is an alkoxylate of an alcohol having an aliphatic group.

12. The process according to claim 1, wherein the viscosity modifier is 2-butoxy-ethanol.

* * * * *